United States Patent
Khuri et al.

(10) Patent No.: US 7,359,743 B2
(45) Date of Patent: Apr. 15, 2008

(54) SYSTEM FOR MONITORING AND CALCULATING INTEGRATED TISSUE PH

(75) Inventors: Shukri F. Khuri, Westwood, MA (US); Edward Meier, Anaheim, CA (US)

(73) Assignee: Terumo Cardiovascular Systems., Ann Arbor, MI (US)

( * ) Notice: Subject to any disclaimer, the term of this patent is extended or adjusted under 35 U.S.C. 154(b) by 0 days.

(21) Appl. No.: 10/554,479

(22) PCT Filed: Dec. 22, 2003

(86) PCT No.: PCT/US03/40799

§ 371 (c)(1),
(2), (4) Date: Sep. 18, 2006

(87) PCT Pub. No.: WO2004/059849

PCT Pub. Date: Jul. 15, 2004

(65) Prior Publication Data

US 2007/0010728 A1    Jan. 11, 2007

(51) Int. Cl.
*A61B 5/05* (2006.01)
*A61B 5/02* (2006.01)
(52) U.S. Cl. ...................................... 600/361; 600/508
(58) Field of Classification Search ................ 600/309, 600/345–366, 508
See application file for complete search history.

(56) References Cited

U.S. PATENT DOCUMENTS

| | | | | |
|---|---|---|---|---|
| 4,774,956 A | * | 10/1988 | Kruse et al. ................. | 600/350 |
| 6,029,076 A | * | 2/2000 | Fiddian-Greene et al. .. | 600/353 |
| 6,165,142 A | * | 12/2000 | Bar ............................. | 600/595 |
| 6,582,365 B1 | * | 6/2003 | Hines et al. ................. | 600/300 |

* cited by examiner

*Primary Examiner*—Charles A. Marmor, II
*Assistant Examiner*—Navin Natnithithadha
(74) *Attorney, Agent, or Firm*—Mark Mollan; Gael Diane Tisack; MacMillian, Sobanski & Todd

(57) ABSTRACT

A system for monitoring tissue pH calculates and displays integrated pH values over one or more user-selectable integration time periods. The values can be displayed in a numerical and/or graphical format. In the graphical format, measured values of pH are displayed as curves. A cursor can be positioned along the curves to display an instantaneous measured value at any point. The integration periods are highlighted relative to the curves. If the cursor is positioned within a region corresponding to an integration period, the display indicates the integrated value of pH from the start of that integration period to the time corresponding to the position of the cursor.

19 Claims, 3 Drawing Sheets

SYSTEM FOR MONITORING AND CALCULATING INTEGRATED TISSUE PH

FIELD OF THE INVENTION

The present invention relates to materials and methods for in vivo detection of hydrogen ion concentration in tissue, calculation of pH, integrating pH values over time, and providing a readout of current and integrated pH. As such, the invention relates to pH measurement and calculation, diagnostic devices, and biomedical devices for monitoring patients.

BACKGROUND OF THE INVENTION

There is a correlation between interstitial pH of cardiac tissue during coronary artery bypass surgery and the resultant postoperative viability of the heart, and consequently the patient. Randolph, J. D. et al., J. Vasc. Sur., 3, No. 2, 216-224 (February 1986); and Khuri et al., J. Thoracic and Cardiovascular Surgery, 86, No. 5, 667-78 (1983).

Khuri et al. concluded that the magnitude of rise in intramyocardial pH and myocardial temperature during the period of aortic cross-clamping is a good indicator of the adequacy of myocardial preservation; and that during periods of aortic cross-clamping exceeding 40 minutes, myocardial temperature is a poor indicator of adequacy of preservation since progressive tissue acidosis may progress despite low myocardial temperatures. Khuri et al. further concluded that techniques and solutions that can effectively reduce the progression of tissue acidosis will likely enhance the clinician's ability to protect the ischemic myocardium during cardioplegic arrest. Khuri 86, at 667; see also Khuri, S. F., Cardiac Surgery: State of the Art Reviews, "Myocardial Preservation During Coronary Artery Bypass Surgery," 1, No. 1, 59-75 (October 1986).

Acidosis is a condition associated with the deprivation of oxygen in the tissue being monitored. Lack of oxygen causes a buildup of hydrogen ions, which can be measured by pH sensors. Preferred pH sensors are described in contemporaneously filed U.S. Application No. 60/434,815, entitled, "Miniature Electrode for Detecting Interstitial Tissue pH", which is incorporated herein by reference. Severe acidosis is associated with a poor prognosis following cardiac bypass surgery.

DETAILED DESCRIPTION

Figure 1:
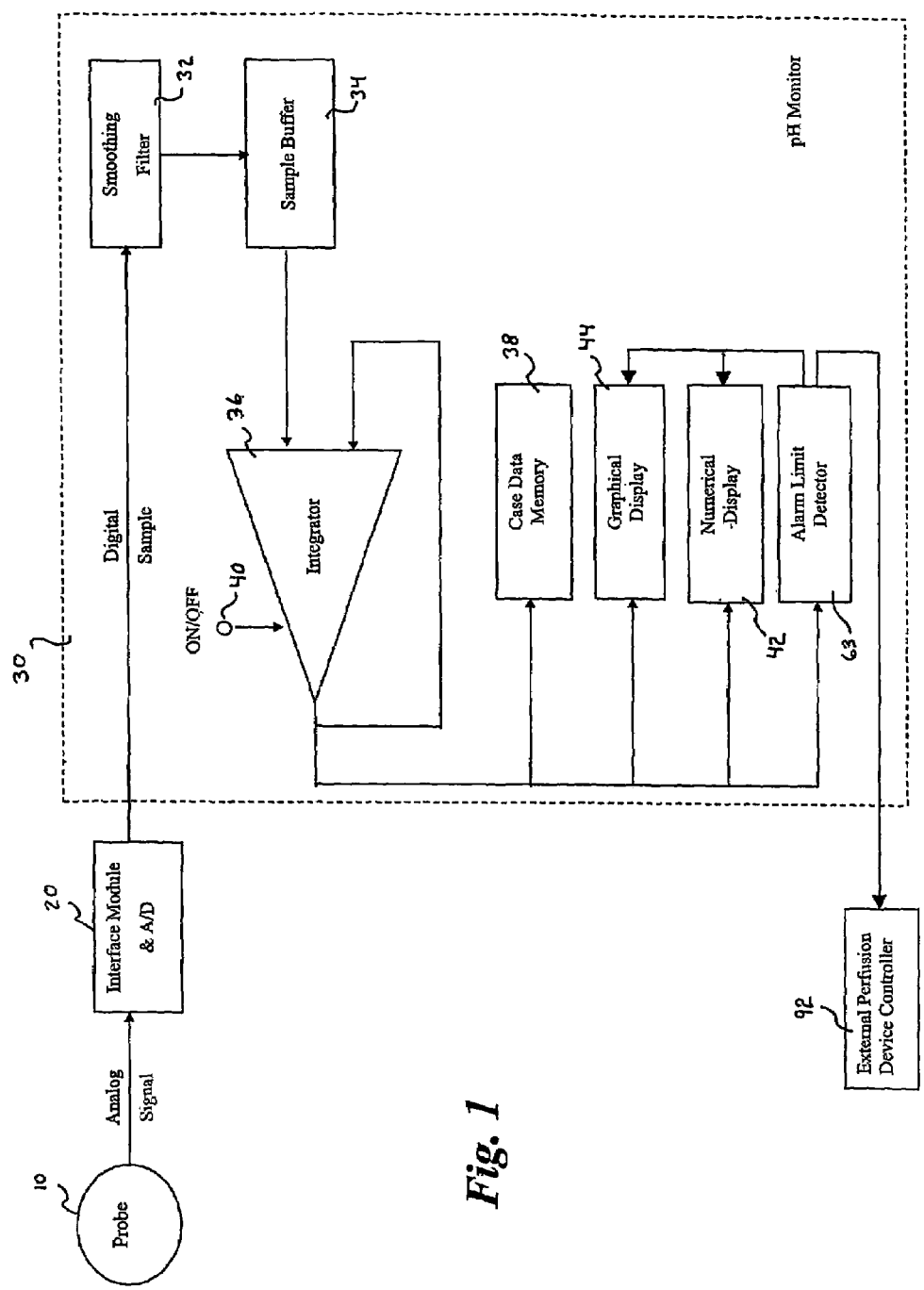
FIG. 1 is a block diagram of a pH monitoring system in which the invention can be implemented.

The continuous collection of pH values in tissue, and integrating those values over time, can best determine the condition of the tissue being evaluated. For example, in the case of cardiac bypass surgery, the myocardial tissue is removed from bloodflow, and acidosis results. The best indicator of long term postoperative prognosis for the tissue, and the patient, is not brief or sudden decreases in pH, but rather a cumulative total of time at reduced pH. Thus, for example, a minor but prolonged decrease in pH can be more damaging than a brief but greater decrease in pH.

The likely damage incurred by the tissue as a result of acidosis is thus a function of both duration and degree. By continuously monitoring the pH of tissue, it is possible to collect data and derive an integrated, or time averaged, pH value. The integrated pH value is a means for assessing the cumulative total decrease in pH over the course of the procedure, e.g., during cross-clamp in the case of coronary bypass surgery. The resulting information can be used to determine preemptively when intervention becomes necessary to protect the ischemic tissue from long-term damage. By integrating pH values from within tissue throughout a time period that includes intermittent treatments, the surgeon can make better decisions about managing the treatment of the tissue and more effectively prevent long term damage to the tissue.

The integrated tissue pH monitoring system of the present invention provides: 1) a mechanism to automatically integrate data representing interstitial pH over a time period defined by the operator; 2) progressive integration points within the total time period; and 3) multiple integration time periods in a single case. Among other things, the present invention provides a system for converting a continuous analog signal derived from an electrochemical determination of the pH of a system to a plurality of digital samples of that signal. The system, through a combination of hardware, firmware, and/or software, is configured to sum the digital samples over time to arrive at an integrated, or time averaged, pH value. The term "integrated pH" is used to refer to a time average value of the pH of a system, and can be calculated according to the equations for determining the time average pH value as presented below.

The resultant integrated pH value can be employed in a system or method for minimizing or eliminating long-term damage to ischemic tissue as a result of surgery, particularly coronary bypass surgery. That is, the integrated pH value can be relied upon by a user to implement prophylactic or remedial measures to eliminate or minimize tissue damage resulting from acidosis. Such prophylactic or remedial measures include perfusion of the tissue with an oxygen vehicle, such as oxygen-rich blood, or by cooling of the tissue, or by other conventional surgical techniques for preventing or eliminating acidosis in ischemic tissue.

Preferred embodiments of the system include one or more display devices such as printouts, gauges, digital readouts, or displays, and/or graphical interfaces such as those commonly employed in biomedical devices and/or other computer based systems or devices. The display device is preferably capable of producing both numeric and graphical representations of the data and calculation results.

In one embodiment, the pH integration function is turned on and off by a switch. In a preferred embodiment, the pH integration function is implemented as a touch screen button press. When the operator activates the integrator, the system keeps a running sum of pH values, starting from the first sample after the switch was turned on. The samples are summed, divided by the number of samples in the integration period, and the result is displayed on the screen. A running value of the integrated pH is displayed according to the following formula:

$$\text{Time } Avg \text{ pH} \atop \text{(during integration)} = \left[ \frac{\sum_{i=start}^{curr} \text{pH}[i]}{((curr - start) + 1)} \right]$$

In a preferred embodiment of the integrated pH monitoring system of the present invention, the system collects all of the pH samples and saves them in a memory device (e.g., a buffer) that can store the entire case called pH[], where pH[1] is the first sample of the case, and pH[curr] is the most recent sample of the case. Within this memory device, the system keeps track of multiple start and stop points for when the operator turns off/on the integrator. When the user activates the integrator, the system saves the location in the buffer of the first point of integration (start), and when the user de-activates the integrator, the system saves the location of the last point (stop). The final value for integrated pH is determined in accordance with the formula shown below, where the integration is the sum of all the pH values between and including pH[start] to pH[stop], divided by the number of samples included within this summation:

$$\text{Time } Avg_{(final)} \text{ pH} = \left[ \frac{\sum_{i=start}^{stop} \text{pH}[i]}{((stop - start) + 1)} \right]$$

If the operator desires another integration region, the system can save a new start value when integration is activated, and save a new stop value when integration is turned off. This allows the user to obtain an infinite number of integration regions during the case. The system allows the operator to view these integration periods independently through the history display in the graphics mode of the operator screen (discussed further below).

The block diagram of FIG. 1 shows how the system of the present invention transforms the raw data from a pH sensor for input into the integrator. A pH probe 10 generates an analog electrical signal based on the pH of the tissue. The probe may be, for example, of the type described in the previously mentioned copending application. The analog electrical signal is amplified and filtered by electronics located in an integrated tissue pH monitoring interface module 20, so that it falls within the input range of the analog-to-digital (A/D) converter located in the module. In addition, the interface module optically isolates the digital signal to prevent any flow of electricity in the direction of the patient. The A/D converter is clocked at a suitable sampling rate, e.g., 10-60 Hz, preferably about 15 Hz, by a monitor 30, which generates a corresponding number of A/D samples per second.

A sampling circuit (not shown) in the monitor gathers the data at the sampling rate, and sequentially passes the samples along to a smoothing filter 32. In an exemplary embodiment, the smoothing filter may operate on a block of data samples, e.g., 10 samples, wherein the filter eliminates aberrant signals (e.g., large or small) and provides an average based on the remaining samples. The smoothing filter 32 repeats this process on each sequential block of data samples. One skilled in the art, however, will readily appreciate that there are a number of ways to implement the smoothing filter. The averaged value is stored in a sample buffer 34, and presented to an integrator 36 to generate a new pH value (pH[curr]) to be stored in a case data memory 38. The algorithm performed in the integrator 36 preferably compensates for the electronics in the interface module, probe differences (calibrated prior to usage of the probes), and temperature.

The integrator 36 can be selectively turned on and off by means of a switch 40. If the operator has the integration function turned on, the system retrieves the next sample and adds it to the current integration. If the integration function is turned off, the integrator ignores the new values being added to the buffer 34. The integrator does not add values to the integration that are out-of-range of the system. Thus, there can be periods of time where the integrator 36 is turned on but is not updating the integrated value because the sampled values are out-of-range. This prevents accidental sensor disconnects from corrupting the entire integration.

The monitor 30 includes a display that provides a visual indication of the measured and integrated values. The display function examines the status of the integration (on/off) and selectively updates the display accordingly. There are two display modes associated with the monitor: numerical 42 and graphical 44. Preferably, the user selects the desired mode. If the monitor is in the numerical mode, the numerical display task 42 grabs the new integrated values at the rate they are being placed in the case data memory 38 (e.g., 1.5 Hz) and updates the screen at that rate. If the integration is off, and has never been turned on, the numerical task displays dashes instead of the integrated pH value. When the integration has been running for at least one sample, and the operator turns the integration off, the numerical display task freezes the final value of the integration and displays it on the screen until the next integration period starts. This frozen value is preferably grayed out or otherwise displayed in a noticeable manner so that the operator can easily see that the integration number is not being updated.

Figure 2:
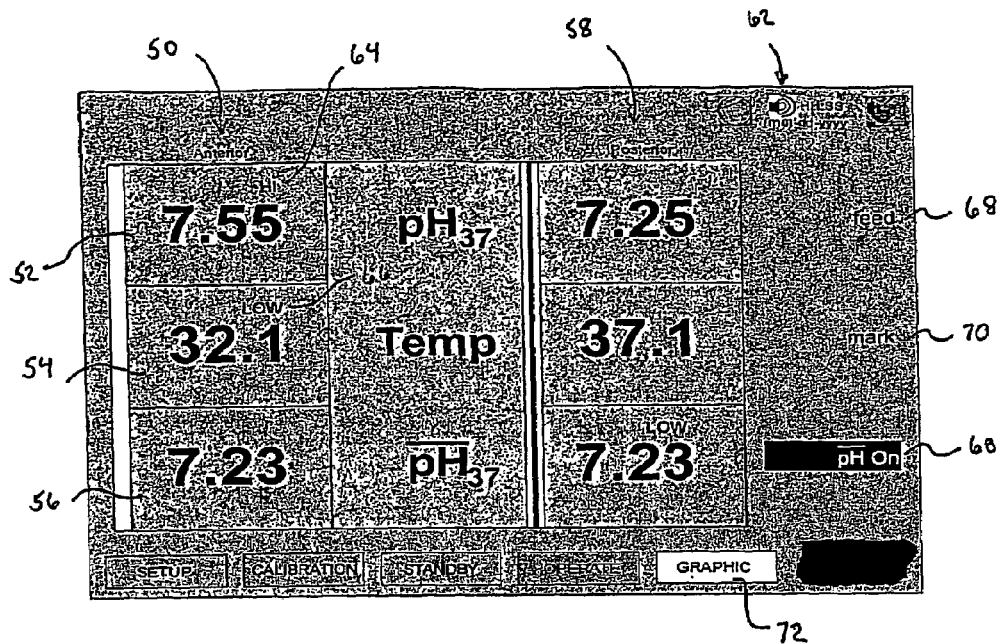
FIG. 2 is an illustration of an exemplary display screen for the numerical display mode.

FIG. 2 illustrates an example of a numerical display. This example pertains to a situation in which two probes, respectively labeled "Anterior" and "Posterior", are employed. In the left column 50, the values of the current pH value 52 (corrected to 37° C.), the temperature 54 and the integrated pH value 56 are displayed for the anterior probe. Similar values for the posterior probe are displayed in the right column 58. In the illustrated example, the ON/OFF switch 40 is turned on, so that integration is currently ongoing, as indicated by the label on the button 60. If the user presses this button (in the case of a touch-screen panel), or otherwise toggles the switch 40, the integrator turns off, and the displayed value 56 freezes. At this time the label on the button 60 changes, for example to "pH Off", and the integrated pH values 56 are preferably grayed out to provide a readily discernible indication that integration has been turned off.

An alarm can be selectively turned on or off, as indicated by the status of an icon 62. When the alarm is on, a detector 63 (FIG. 1) compares the measured and integrated values with limits determined by the user. If any of the displayed values lies outside of a user-determined limit, an indicator is displayed adjacent that value. In addition, an audible alarm can be generated, to direct the user's attention to the display. In the example of FIG. 2, an alarm indicator 64 is displayed adjacent the current pH value 52 to alert the user that the value is above the pre-set limit, and an indicator 66 is displayed adjacent the temperature value 54 to provide an alert that it is too low. When a displayed value is in an alarm state, the background for that value can flash as a further means of gathering the user's attention.

Other buttons can be displayed on the screen. A "feed" button 68 allows the user to advance paper out of an associated printer. A "mark" button 70 enables the user to put an indexed mark on data stored in the memory 38, to identify significant events during a surgical procedure, such as clamp on, delivery of cardioplegia, etc. A display mode button 72 toggles between the numeric and graphic modes.

Figure 3:
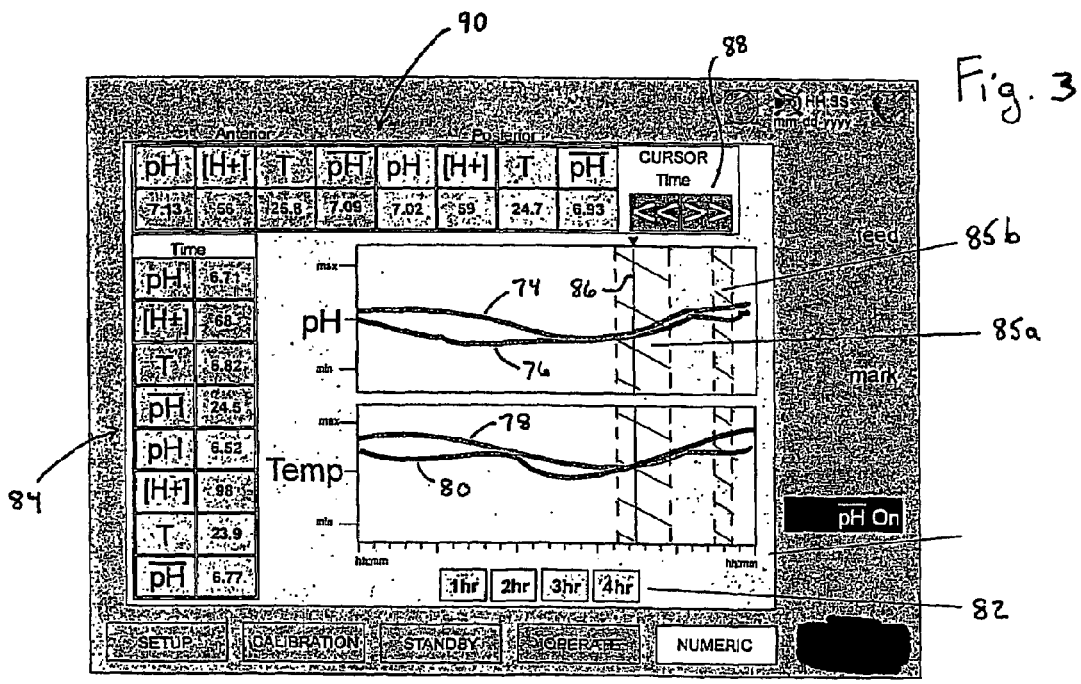
FIG. 3 is an illustration of an exemplary display screen for the graphical display mode.

The graphical display mode provides the most information about the integration, with the ability to view multiple integration periods. Referring to FIG. 3, a pair of curves or traces 74, 76 display the measured pH values for the respective anterior and posterior probes. Likewise, the measured temperature values for the two probes are represented by a pair of respective curves 78, 80. The time scale for the curves can be adjusted by a set of zoom buttons 82. The current values 84 for each of the measured parameters are displayed on the left side of the screen. Preferably, the values for the anterior and posterior probes are displayed with different respective background colors, and the curves 74-78 are displayed with the same respective colors to facilitate ready correlation of the numerical values with the curves. The integration periods, i.e., the times during which the switch 40 is ON, are indicated by highlighted regions 85*a* and 85*b* (indicated by the shaded areas).

The graphic mode provides the user with a cursor 86 that can be moved to any point on the graph by means of arrow buttons 88. The historical values at the point denoted by the cursor are displayed in a numerical format 90 above the curves 74-80. If the user places the cursor 86 within an integration period 85, the historical values 90 display the integrated pH numbers from the start of the integration (i.e., pH[start]) to the selected point, giving the user access to any integration point within the full range of the integration period. The user can scroll the cursor to the end of the integration period (pH[stop]), and get the final integration value for the desired integration period. If the user places the scroll bar in a region that is not within an integration period, the integrated pH value is represented as dashes.

Alarm indicators can also be employed in the graphical mode. For example, if a value is outside an acceptable limit, it can be displayed with a contrasting background color to catch the user's attention, e.g., bright red, and/or flashed.

Figure 4:
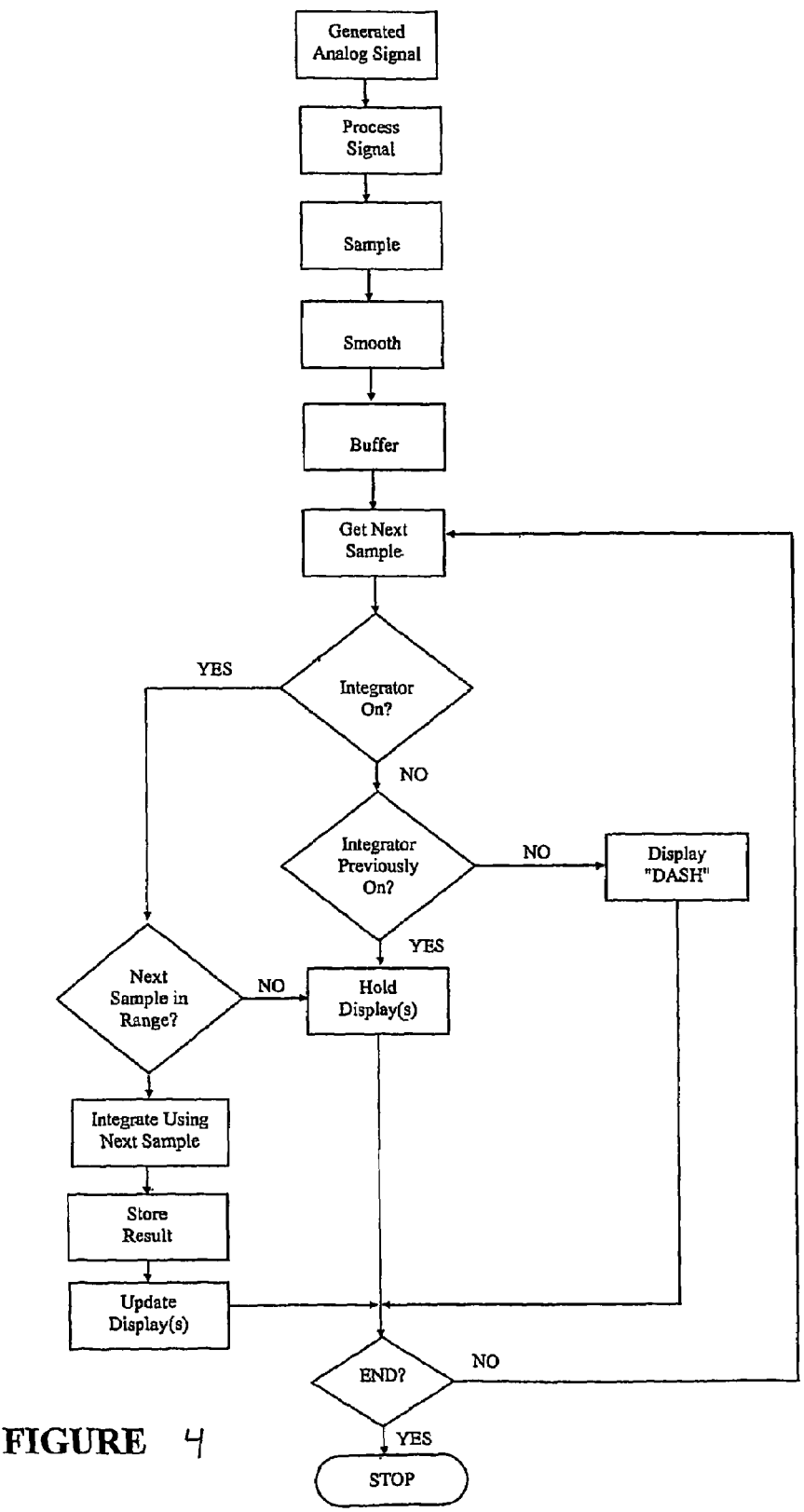
FIG. 4 is flow chart of the operation of the pH monitoring system.

FIG. 4 is a block diagram illustrating a method for achieving integrated pH values. It will be understood that the method steps illustrated in FIG. 4 are exemplary.

Optionally, the processing unit can be electrically integrated with other biomedical devices to instantaneously address the condition causing the aberrant readings. Thus, for example, where the alarm limit detector determines that the integrated pH of the tissue is below the pre-determined range, a controller 92 can be instructed to activate a pump to perfuse the tissue with oxygenating fluid, thereby raising the pH of the tissue to an acceptable level. When the detector 63 determines that the pH of the tissue has been restored to the acceptable range, it causes the controller 92 to terminate the operation of the pump. Similarly, if the temperature is too low, the controller 92 can activate a heater until the temperature returns to a suitable value.

It will be understood that the foregoing description and examples are presented merely for illustration of the present invention, and are not intended to limit the scope of protection afforded the invention.

What is claimed is:

1. A system for monitoring the pH of a patient's cardiac tissue, comprising:
   a probe that measures the pH value of a patient's cardiac tissue;
   an integrator that determines an average value of the measured pH value over a period of time that includes intermittent treatments;
   a display device that displays the integrated value; and
   a manually actuated switch that selectively activates and deactivates said integrator during the intermittent treatments to thereby define said period of time.

2. The system of claim 1, wherein said display device displays said integrated value in a numerical form.

3. The system of claim 2 wherein, when said integrator is activated, said display device dynamically displays current, running values for the integrated value.

4. The system of claim 3 wherein, when said integrator is deactivated, said display device statically displays the last value calculated by the integrator before it was deactivated.

5. The system of claim 2, wherein said display device also displays the measured value in the form of a graphical trace.

6. The system of claim 5, further including a cursor that can be manually positioned along said graphical trace.

7. The system of claim 6 wherein said display device includes a first numerical display of a current measured value and a second display of a measured value at the location of the cursor on a graphical trace.

8. The system of claim 6 wherein said display device indicates a region associated with said traces that corresponds to an integration time period.

9. The system of claim 8 wherein, when said cursor is positioned within said region, the display device displays a numerical value indicating the integrated value from the start of the integration time period to which said region corresponds until the time on a trace corresponding to the location of the cursor.

10. The system of claim 8, wherein said display device displays multiple regions corresponding to multiple respective integration time periods.

11. The system of claim 2 further including a limit detector which compares at least one of the measured value and the integrated value to a preset limit value, and which generates an alarm indicator when the compared value lies outside of the limit value.

12. The system of claim 11, wherein said alarm indicator comprises an alphanumeric indicator adjacent the displayed value.

13. The system of claim 11, wherein said alarm indicator comprises a distinctly colored background for the displayed value.

14. The system of claim 11, wherein said alarm indicator comprises a flashing background for the displayed value.

15. The system of claim 11, wherein said alarm indicator comprises an audible sound.

16. The system of claim 11 further including a controller that is responsive to said detector for actuating a biomedical device when the compared value lies outside of the limit value.

17. The system of claim 16 wherein said biomedical device is a perfusion pump.

18. The system of claim 16 wherein said biomedical device is a heater.

19. A method of monitoring the pH of a patient's cardiac tissue over a period of time that includes intermittent treatments, comprising the steps of:
   inserting a probe for monitoring pH into a patient's cardiac tissue;
   maintaining an average pH value in an integrator;
   manually actuating a switch from an off state to an on state during the intermittent treatments and manually actuating the switch from the on state to the off state when the intermittent treatments are suspended to thereby define the period of time;
   repeatedly sampling a pH value from the probe;
   when the switch is in the off state, then ignoring each sampled pH value;
   when the switch is in the on state, then updating the average pH value in the integrator in response to each sampled pH value; and
   displaying the average pH value such that the last value calculated by the integrator is displayed when the switch is in the off state.

* * * * *